United States Patent
Li et al.

(10) Patent No.: US 11,237,092 B2
(45) Date of Patent: Feb. 1, 2022

(54) SANDBOX TEST SYSTEM AND METHOD FOR KARST AQUIFER BASED ON TRACER-HYDRAULIC TOMOGRAPHY INVERSION

(71) Applicant: SHANDONG UNIVERSITY, Shandong (CN)

(72) Inventors: Shucai Li, Jinan (CN); Zhenhao Xu, Jinan (CN); Xintong Wang, Jinan (CN); Peng Lin, Jinan (CN); Dongdong Pan, Jinan (CN); Wenyang Wang, Jinan (CN); Yichi Zhang, Jinan (CN)

(73) Assignee: SHANDONG UNIVERSITY, Shandong (CN)

( * ) Notice: Subject to any disclaimer, the term of this patent is extended or adjusted under 35 U.S.C. 154(b) by 0 days.

(21) Appl. No.: 17/253,382

(22) PCT Filed: Oct. 17, 2019

(86) PCT No.: PCT/CN2019/111752
§ 371 (c)(1),
(2) Date: Dec. 17, 2020

(87) PCT Pub. No.: WO2021/017195
PCT Pub. Date: Feb. 4, 2021

(65) Prior Publication Data
US 2021/0223156 A1 Jul. 22, 2021

(30) Foreign Application Priority Data

Jul. 30, 2019 (CN) .......................... 201910695296.6
Aug. 14, 2019 (CN) .......................... 201910749164.7

(51) Int. Cl.
*G01N 15/08* (2006.01)
*G01N 33/24* (2006.01)
*G09B 23/40* (2006.01)

(52) U.S. Cl.
CPC ..... *G01N 15/0806* (2013.01); *G01N 15/0826* (2013.01); *G01N 33/24* (2013.01); *G09B 23/40* (2013.01)

(58) Field of Classification Search
CPC .... G01N 15/00; G01N 15/08; G01N 15/0806; G01N 15/0826; G01N 33/00; G01N 33/24; G09B 23/40
See application file for complete search history.

(56) References Cited

U.S. PATENT DOCUMENTS 10,338,273 B2 * 7/2019 Wang ................... G01V 99/005
10,989,702 B2 * 4/2021 Li .......................... G09B 23/40
2017/0306282 A1 10/2017 Hewitt et al.

FOREIGN PATENT DOCUMENTS

CN 103345867 A 10/2013
CN 103994951 A 8/2014
(Continued)

OTHER PUBLICATIONS

Apr. 24, 2020 Search Report issued in International Patent Application No. PCT/CN2019/111752.
(Continued)

*Primary Examiner* — Nguyen Q. Ha
(74) *Attorney, Agent, or Firm* — Oliff PLC

(57) ABSTRACT

A sandbox test system and method for a karst aquifer based on tracer-hydraulic tomography inversion, including a visual sandbox apparatus, a karst conduit, a water flow control apparatus, a horizontal well, a data acquisition apparatus, and a data processing apparatus. The visual sandbox apparatus forms a sand layer packing space. The karst conduit is buried in a sand layer. The water flow control apparatus is a (Continued)

constant water head storage tank. A back plate is provided with a horizontal well mounting hole and tracer adding hole. The horizontal well is mounted in each horizontal well mounting hole. A monitoring well is connected to a seepage pressure sensor or an electrical conductivity sensor. A water injection and pumping well is connected to a peristaltic pump. The electrical conductivity sensor, seepage pressure sensor, and peristaltic pump connect to the data acquisition apparatus. The data acquisition apparatus connects to the data processing apparatus.

9 Claims, 3 Drawing Sheets

(56) References Cited

FOREIGN PATENT DOCUMENTS

| CN | 104282214 A | | 1/2015 | |
|----|-------------|---|--------|---|
| CN | 106324226 A | | 1/2017 | |
| CN | 108088982 A | * | 5/2018 | ............... G01N 1/28 |
| CN | 108196006 A | | 6/2018 | |
| CN | 109060598 A | | 12/2018 | |

OTHER PUBLICATIONS

Apr. 24, 2020 Written Opinion of the International Searching Authority issued in International Patent Application No. PCT/CN2019/111752.

* cited by examiner

SANDBOX TEST SYSTEM AND METHOD FOR KARST AQUIFER BASED ON TRACER-HYDRAULIC TOMOGRAPHY INVERSION

BACKGROUND

Technical Field

The present invention relates to an indoor sandbox test system and method for karst aquifer based on hydraulic tomography inversion.

Related Art

The description in this section merely provides background information related to the present disclosure and does not necessarily constitute the prior art.

Karst aquifer plays an important role in industrial, agricultural, and drinking water supplies. It is estimated that 25% of the population in the world depend on karst water resources. In addition, hydraulic transmission parameters of a karst aquifer play an important role in many aspects of various fields such as geoscience and civil engineering. For example, the permeability and porosity control solutes and energy migration of the aquifer, and the like. Hydraulic parameter values and spatial distribution of a karst aquifer play an important role in studies such as underground engineering design, petroleum and natural gas exploration, nuclear waste disposal, underground energy storage, and groundwater pollution evaluation and remediation. Karst aquifers are highly inhomogeneous and heterogeneous, and have diverse spatial scales. Consequently, it is a great challenge to explore a karst conduit pattern as well as its position and distribution in karst limestone.

The inventor finds that the most direct method of determining structural features of a conduit is on-site mapping or to step directly into a karst cave. However, the method is difficult to implement and has high costs. Currently, a water injection and pumping test is getting popular owing to its high operability. Therefore, it is necessary to study, through an indoor test, features of water head response in karst aquifer to precipitation or water injection during the water injection and pumping test, and to conduct a structure inversion research based on the water head change. Currently, there is an urgent need of an indoor test apparatus to simulate water injection and pumping of the water-bearing medium of the karst conduit.

SUMMARY

To resolve the problem above, the present invention provides an indoor sandbox test system and operation method for karst aquifer based on tracer-hydraulic tomography inversion.

To achieve the objective, the following technical solutions are used in the present invention:

A sandbox test system for a karst aquifer based on tracer-hydraulic tomography inversion includes:

a visual sandbox apparatus, a karst conduit, a water flow control apparatus, a horizontal well, a data acquisition apparatus, and a data processing apparatus;

the visual sandbox apparatus includes a back plate, a front plate, porous water permeable plates, a constant water head storage tank, and a base; the back plate and the front plate are mounted on the base in a parallel manner; two constant water head storage tanks are provided, respectively mounted on a left side and a right side of the back plate and the front plate, and the porous water permeable plates are mounted between the constant water head storage tank and the back plate and between the water head storage tank and the front plate; the back plate, the front plate, the porous water permeable plates, and the base define a sand layer packing space; and the karst conduit is buried in the sand layer;

the water flow control apparatus supplies water for the constant water head storage tanks, to control water volumes of the two constant water head storage tanks; and the back plate is provided with a horizontal well mounting hole and a tracer adding hole; a horizontal well is mounted in each horizontal well mounting hole, some of the horizontal wells are used as monitoring wells, and some of the horizontal wells are used as water injection and pumping wells; the monitoring well is connected to a seepage pressure sensor or an electrical conductivity sensor; the water injection and pumping well is connected to a peristaltic pump; the electrical conductivity sensor, the seepage pressure sensor, and the peristaltic pump are connected to the data acquisition apparatus; and the data acquisition apparatus is connected to the data processing apparatus.

In a further technical solution, the overflow tank includes a first overflow tank and a second overflow tank, both an inlet of the first overflow tank and an inlet of the second overflow tank are connected to a water supply apparatus, an outlet of the first overflow tank is connected to the constant water head storage tank on the left side, and an outlet of the second overflow tank is connected to the constant water head storage tank on the right side.

In a further technical solution, the first overflow tank is mounted on a first height adjustment apparatus and the second overflow tank is mounted on a second height adjustment apparatus.

In a further technical solution, each horizontal well includes an inner sleeve and an outer sleeve that are open at both ends, the inner sleeve is mounted in the outer sleeve, and the two sleeves are connected through a reducing bushing; a side wall of the outer sleeve is provided with a plurality of water inlet holes, and a sand prevention mesh is adhered to an inner wall of the outer sleeve to prevent sand particles from entering the horizontal well, destroying an aquifer structure, and blocking the horizontal well to hinder data monitoring; and the outer sleeve is provided with a plug, the plug is provided with a stainless steel tube that is connected to an external hose, and the hose is further connected to the seepage pressure sensor.

In a further technical solution, the karst conduit includes three types: a branch conduit karst structure, a pool karst structure, and a waterfall karst structure. The technical solution can implement construction of a complex karst aquifer and set a foundation for exploration of the heterogeneity of karst structures.

In a further technical solution, a sand prevention mesh is adhered to one side of the porous water permeable plate to prevent sand particles from entering the constant water head storage tank.

A method for simulating a natural flow and solute migration of an unconfined aquifer in a controlled laboratory environment by using the apparatus above includes the flowing steps:

1) sieving testing sand according to required particle sizes and a required combination of the particle sizes;

2) pre-fabricating a heterogeneous sand layer and the karst conduit, and hierarchically performing filling and compaction;

3) sequentially mounting the horizontal wells and performing coring, connecting the monitoring well to the seepage pressure sensor or the electrical conductivity sensor, and connecting the water injection and pumping well to the peristaltic pump, water leakage prevention measures being required at joints;

4) connecting the seepage pressure sensor, the electrical conductivity sensor, and the peristaltic pump to the data acquisition apparatus; connecting the data acquisition apparatus to the data processing apparatus, switching on a water source to supply water for the overflow tank, and performing water leakage check;

5) adjusting the height of the overflow tank to ensure a steady water head on a boundary, setting a boundary condition determined by a working condition, calibrating the seepage pressure sensor and the electrical conductivity sensor, and debugging the peristaltic pump;

adjusting the peristaltic pump, controlling the water injection and pumping speed, turning on the sensor before pumping each time, that is, before the peristaltic pump operates, and monitoring and collecting water head data in advance, to obtain an initial water head at a pumping port; pumping at the horizontal well during the test, simultaneously starting head monitoring to record an instantaneous water head change, turning on the peristaltic pump, then turning off the peristaltic pump once a steady flow state is reached, and monitoring and collecting water head recovery data;

6) adjusting water heads on two sides to form a particular water head difference, putting a tracer at a leftmost port, and monitoring electrical conductivity in the middle and on the right side of the sandbox; and 7) recording and detecting dynamic changes of data through a central processing unit, and forming a graph in real time, analyzing a test result, and finally conducting a karst structure inversion analysis with reference to program development.

An operation method for simulating a natural flow and solute migration of an unconfined aquifer in a controlled laboratory environment by using the apparatus above includes the flowing steps:

1) sieving testing sand according to required particle sizes and a required combination of the particle sizes;

2) pre-fabricating a heterogeneous sand layer and the karst conduit, and hierarchically performing filling and compaction;

3) sequentially mounting the horizontal wells and performing coring, connecting the monitoring well to the seepage pressure sensor or the electrical conductivity sensor, and connecting the water injection and pumping well to the peristaltic pump, water leakage prevention measures being required at joints;

4) connecting the sensors and the peristaltic pump to the data acquisition device and the central processing unit, switching on a water source to supply water for the overflow tank, and performing water leakage check.

5) adjusting the height of the overflow tank to ensure a steady water head on a boundary, setting a boundary condition determined by a working condition, calibrating the seepage pressure sensor and the electrical conductivity sensor, and debugging the peristaltic pump; adjusting the peristaltic pump, controlling the water injection and pumping speed, turning on the sensor 2 min before pumping each time, that is, before the peristaltic pump operates, and monitoring and collecting water head data in advance, to obtain an initial water head at a pumping port. pumping at the horizontal well during the test, simultaneously starting head monitoring to record an instantaneous water head change, turning on the peristaltic pump, then turning off the peristaltic pump once a steady flow state is reached, and monitoring and collecting water head recovery data;

6) adjusting water heads on two sides to form a water head difference, putting a tracer at a leftmost port, and monitoring electrical conductivity in the middle and on the right side of the sandbox, where Nacl is used as an example for research in the present invention;

7) recording and detecting dynamic changes of data through a central processing unit, and forming a graph in real time, analyzing a test result, and finally conducting a karst structure inversion analysis with reference to program development.

In the present invention, specific settings are made according to different aquifer status and boundary conditions, steps (1) to (3) are repeated to control a flowmeter and well status, steps (4) to (6) are repeated, and a practical project is guided according to different results obtained in step (7).

The present invention conducts research on an indoor sandbox test system and operation method for karst aquifer based on tracer-hydraulic tomography inversion, to overcome shortcomings such as a long time and high costs of a field test and implement a more real simulation of a karst conduit aquifer with an indoor adjustment, thereby being more practical and integrate. Compared with the research afore, the apparatus of the present invention has the following advantages.

1) Through a visual sandbox system of the present invention, solute migration in a sandbox can be observed visually and the flow feature of a karst conduit aquifer can be simulated. The sandbox system is easy to assemble and can be reused.

2) A heterogeneous karst system of the present invention creatively introduces different conduit structures into the sand layer, to implement construction of a complex karst aquifer, laying a foundation for exploration of the heterogeneity of karst structures.

3) A controllable flow boundary system of the present invention can build a constant head boundary to quickly and effectively supply water along the length and thickness of the entire aquifer, which simulates a working condition more authentically. The controllable flow boundary system has strong adaptability and is easy to operate, facilitating adjustment of a boundary water head.

4) A horizontal well pumping system of the present invention can implement water injection and pumping with a single well head or with a plurality of well heads in collaboration according to requirements of different water injection and pumping tests, and can adjust water injection and pumping conditions in real time according to a specific working condition.

5) In the present invention, data is collected by using the seepage pressure sensor and the electrical conductivity sensor, implementing all-around and multi-data monitoring in real time, and also implementing automatic data collection and recording, adjustment of the speed of the peristaltic pump, and sensor calibration.

6) The data processing apparatus of the present invention can perform analysis and feedback processing on collected pressure and electrical conductivity data in time, form a graph in real time, and conduct a karst structure inversion analysis with reference to program development.

BRIEF DESCRIPTION OF THE DRAWINGS

The accompanying drawings constituting a part of this application are used for providing further understanding for this application. Exemplary embodiments of this application and descriptions thereof are used for explaining this application and do not constitute any inappropriate limitation to this application.

Figure 1:
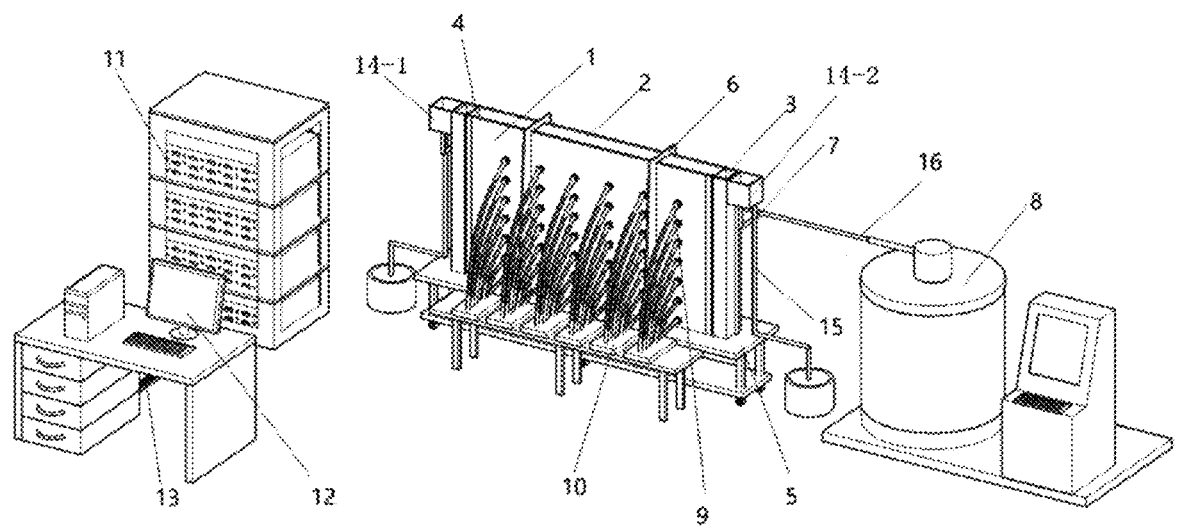
FIG. 1 is a schematic diagram of a test apparatus according to the present invention.
Figure 2:
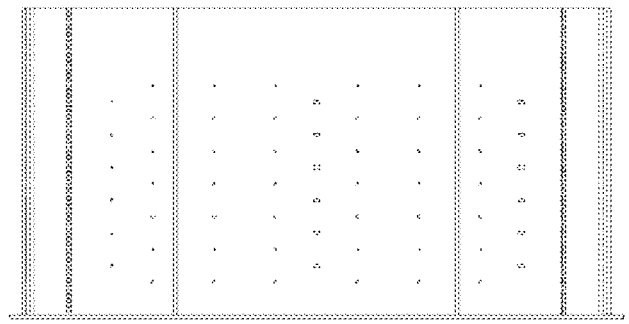
FIG. 2, FIG. 3, and FIG. 4 are two-dimensional diagrams of a visual sandbox system.
Figure 3:
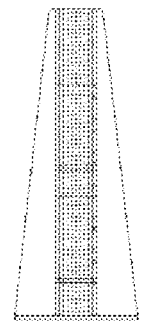
Figure 4:
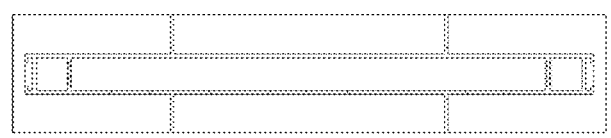

In the drawings: 1. front plate; 2. back plate; 3. storage tank; 4. porous water permeable plate; 5. base; 6. supporting frame; 7. connection hose; 8. water supply apparatus; 9. horizontal well; 10. data acquisition device; 11. central processing unit; 12. display; 13. transmission line; 14-1. overflow tank; 14-2. overflow tank; 15. adjustable lifting rod; 16. water supply pipe.

DETAILED DESCRIPTION

It is to be noted that the following detailed descriptions are all exemplary and are intended to provide a further understanding of this application. Unless otherwise specified, all technical and scientific terms used herein have the same meaning as commonly understood by those of ordinary skill in the art to which this application belongs.

It is to be noted that terms used herein are only for describing specific implementations and are not intended to limit exemplary implementations according to this application. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

For convenience of description, the words "above", "below", "left", and "right" only indicate directions consistent with those of the accompanying drawings, are not intended to limit the structure, and are used only for ease and brevity of illustration and description, rather than indicating or implying that the mentioned device or element must have a particular orientation or must be constructed and operated in a particular orientation. Therefore, such terms should not be construed as a limitation on the present invention.

For the part of term explanation, terms in the present invention such as "mount", "connect", "connection", and "fix" should be understood in a broad sense. For example, the connection may be a fixed connection, a detachable connection, or an integral connection, a mechanical connection, an electrical connection, a direct connection, an indirect connection by using an intermediate medium, an interior connection between two components, or interaction between two components. A person of ordinary skill in the art may understand specific meanings of the foregoing terms in the present invention according to a specific situation.

As introduced in the part of related art, the most direct method of determining structural features of a conduit in the related art is on-site mapping or to step directly into a karst cave. However, the method is difficult to operate and has high costs. Currently, a water injection and pumping test is getting popular owing to its high operability. Therefore, it is necessary to study, through an indoor test, features of water head response in karst aquifer to precipitation or water injection during the water injection and pumping test, and to conduct a structure inversion research based on the water head change. Currently, there is an urgent need of an indoor test apparatus to simulate water injection and pumping of the water-bearing medium of the karst conduit.

To resolve the technical problem above, the present invention provides a sandbox test system and method for karst aquifer based on tracer-hydraulic tomography inversion.

In a typical implementation of the present invention, an indoor sandbox test system for karst aquifer based on tracer-hydraulic tomography inversion, as shown in FIG. 1, includes a visual sandbox system, a heterogeneous karst system, a controllable flow boundary system, a horizontal well pumping system, a data acquisition and control system, and an information analysis system.

Specifically, the visual sandbox system includes a front plate 1, a back plate 2, a constant water head storage tank 3, porous water permeable plates 4, a base 5, and a supporting frame 6.

The back plate 2 and the front plate 1 are mounted on the base 5 in a parallel manner. There are two constant water head storage tanks 3, respectively mounted on a left side and a right side of the back plate and the front plate. The porous water permeable plates are mounted between the constant water head storage tank and the back plate, and between the constant water head storage tank and the front plate. The back plate, the front plate, the porous water permeable plates, and the base define a sand layer packing space. The karst conduit is buried in the sand layer. The main body of the visual sandbox system is a model body of a visual cuboid sandbox. The test sandbox is mainly used for simulating the flow and a solute migration feature of a two-dimensional aquifer. In this embodiment, the external size of the sandbox is 140 cm in length, 12 cm in width, and 75 cm in height, and the internal size is 120 cm*10 cm*64 cm.

The base 5 and the supporting frame 6 on two sides are formed by welded angle iron. The supporting frame 6 is in a triangle shape. Vertical angle iron is fixed by a bolt at an overlap to ensure the structural stability and integrity.

A test bench frame is formed by welding stainless steel square tubes. The size may be designed as 150 cm*60 cm*50 cm (length*height*width). Each of casters is a universal wheel with a fixing foot for convenience of movement.

The constant water head storage tanks 3 are located on two sides, and are provided with holes at the bottom to be externally connected to the overflow tanks 14, to provide a steady water head boundary.

Two porous water permeable plates 4, including a porous organic glass plate and a 160-mesh stainless steel sand screen, are disposed between the constant water head storage tanks and a sand body. The stainless steel cloth is adhered to the porous plates 4 by corrosion resistant epoxy resin to prevent sand particles from entering the tank through the glass plate.

The front plate 1 and the back plate 2 of the sandbox are all organic glass plates, which are transparent and visible. Through the organic glass plates, a sand layer change can be observed and photographed during the test. A back monitoring wall is provided with several ports that are mainly used for data collection, including sediment coring, mounting of the horizontal well 9, provision of a pumping port, medicament administration, and arrangement and connection of a seepage pressure sensor and an electrical conductivity sensor. Diameters of the ports may be set according to actual requirements, for example, according to the size of the horizontal well.

In addition, a stainless steel part is welded at a joint to provide a water-proof seal. A neoprene strip is stuck into a side seam of the stainless steel part to fill the seam. A flame retardant polyurethane adhesive is then used to cover the seam to achieve corrosion resistance. An adhesive is used to fill a seam between the glass and the stainless steel.

Figure 5:
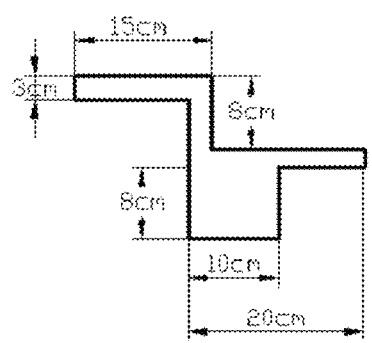
FIG. 5 is a schematic diagram of a branch conduit karst structure.
Figure 6:
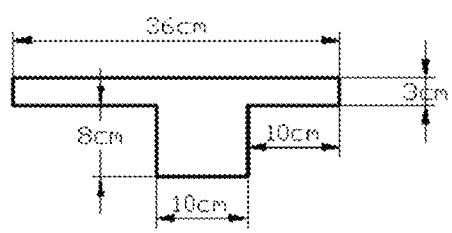
FIG. 6 is a schematic diagram of a pool karst structure.
Figure 7:
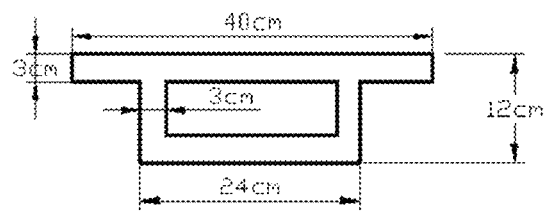
FIG. 7 is a schematic diagram of a waterfall karst structure.

The heterogeneous karst system includes a plurality of sand layers and a plurality of types of karst structures. Specific karst structures are shown in FIG. 5, FIG. 6 and FIG. 7, mainly including three types: a branch conduit karst structure, a pool karst structure, and a waterfall karst structure. The heterogeneous karst system can implement construction of a complex karst aquifer, and set a foundation for exploration of the heterogeneity of karst structures.

Any one, any two, or all of the branch conduit karst structure, the pool karst structure, and the waterfall karst structure may be set in the sand layers. Specific layout may also be at random to better simulate actual status of a karst aquifer.

The controllable flow boundary system includes an overflow tank 14-1, an overflow tank 14-2, a connection hose 7, and a water supply apparatus 8, to facilitate adjustment of a boundary water head. Both an inlet of the overflow tank 14-1 and an inlet of the overflow tank 14-2 are connected to the water supply apparatus 8. An outlet of the overflow tank 14-1 is connected to the constant water head storage tank on the left side and an outlet of the overflow tank 14-2 is connected to the constant water head storage tank on the right side.

The overflow tank 14-1 is mounted on a first height adjustment apparatus and the overflow tank 14-2 is mounted on the second height adjustment apparatus, which facilitates control of sizes of heads of the two overflow tanks and a water level difference between the constant water head storage tanks.

The constant water head storage tanks 3 are located on the two sides of the sand body. The bottom of the constant water head storage tank is provided with a hole to be externally connected, through the connection hose 7, to the two overflow tanks and the water supply apparatus 8, to provide a steady water head boundary.

The overflow tank 14 is connected to a water source, and is connected to a water supply pipe 16, the connection hose 7, and the water supply apparatus 8.

Figure 8:
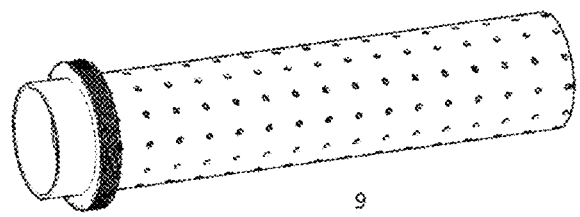
FIG. 8 is a schematic diagram of a horizontal well.
Figure 9:
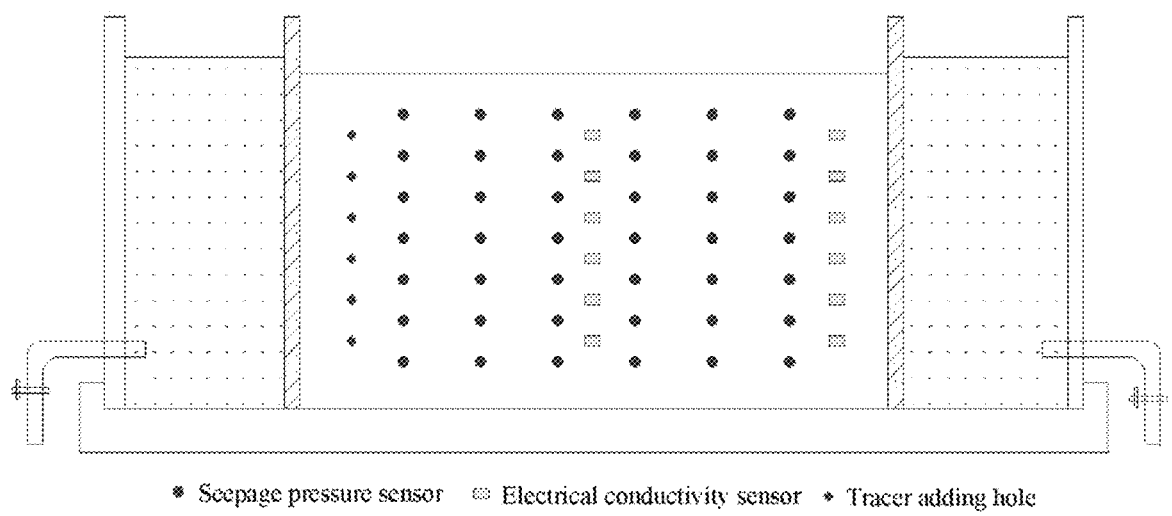
FIG. 9 is a schematic diagram of an arrangement of sensors.

The water injection and pumping well, responsible for simulating a water injection and pumping environment, includes horizontal wells 9, a reducing bushing, a peristaltic pump, a digital display flowmeter, and the like. The horizontal wells 9 are divided into two types based on functions: monitoring well and water injection and pumping well. The monitoring well is mainly connected to a monitoring element, and the water injection and pumping well is mainly connected to the peristaltic pump. Structures of the two wells are identical and the only difference lies in connection parts. The structure of the horizontal well 9, as shown in FIG. 8, includes thin-walled organic glass sleeves. The sleeves include an inner sleeve and an outer sleeve. The length of the inner sleeve is about 15 cm and the diameter thereof is 0.7 cm. The length of the outer sleeve is about 9 cm and the diameter thereof is 0.9 cm. An inner wall of the outer sleeve is wrapped by a 160-mesh stainless steel sand screen with corrosion resistant epoxy resin as a paste to prevent sand particles from entering the horizontal well, destroying an aquifer structure, and blocking the horizontal well to hinder data monitoring.

The diameter of the inner sleeve is slightly less than that of the outer sleeve and is used as a sediment core extractor. The inner and outer sleeves are connected through the reducing bushing. The inner sleeve is nested in the outer sleeve. The reducing bushing is a brass joint, which is connected to the port of the back monitoring wall, provided with a screw, and externally connected to the hose and the seepage pressure sensor, or the electrical conductivity sensor, or the peristaltic pump.

The measuring range of the peristaltic pump is 300 mL/min. The peristaltic pump is connected to the digital display flowmeter, and provides an adjustable flow rate. Different rates may be set for pumping.

The seepage pressure sensor is responsible for monitoring a groundwater water head change, the brand of which is CFSensor. The seepage pressure sensor has a measuring range of 10 KPa and precision of 0.1%. The seepage pressure sensor, externally connected to a data acquisition device, has a 4-20 mA output function.

The data acquisition and control system includes the seepage pressure sensor and a 72-channel data acquisition device 10. The sensor and a gauge are connected to a central processing unit 11, and can monitor a permeation pressure change during the test. The information analysis system includes the central processing unit 11, a display 12 and a transmission line 13, to perform data analysis and feedback processing.

The data acquisition device is a 9-path acquisition device 10, each path being provided with 8 channels. There are a total of 72 channels. The central processing unit 11 is Siemens 57-200SMART. The data acquisition device 10 is connected to a programmable logical controller (PLC) module in the central processing unit 11. Data is processed by analytical control software installed on the PLC module. The software is provided with an automatic pressure calibration method.

A method for simulating a natural flow and solute migration of an unconfined aquifer in a controlled laboratory environment by using the apparatus above includes the flowing steps:

1) Sieve testing sand according to required particle sizes and a required combination of the particle sizes.

2) Pre-fabricate a heterogeneous sand layer and the karst conduit, and hierarchically perform filling and compaction.

3) Sequentially mount the horizontal wells 9 and perform coring; specifically, insert the horizontal well into the sandbox from the port until the horizontal well presses against the other side plate; pull out the inner sleeve together with a sand core therein to complete coring; then plug the outer sleeve with a plug, and connect stainless steel tube on the plug to the external hose and the seepage pressure sensor. Connect the monitoring well to the seepage pressure sensor and the electrical conductivity sensor, and connect the water injection and pumping well to the peristaltic pump, water leakage prevention measures being taken at joints.

4) Connect the sensors and the peristaltic pump to the data acquisition device and the central processing unit 11, switch on a water source to supply water for the overflow tank 14, and perform water leakage check.

5) Adjust the height of the overflow tank to ensure a steady water head on a boundary, set a boundary condition determined by a working condition, calibrate the seepage pressure sensor and the electrical conductivity sensor, and debug the peristaltic pump. Adjust the peristaltic pump, control the water injection and pumping speed, turn on the sensor 2 min before pumping each time, that is, before the peristaltic pump operates, and monitor and collect water head data in advance, to obtain an initial water head at a pumping port. Pump at the horizontal well during the test, simultaneously start head monitoring to record an instantaneous water head change, turn on the peristaltic pump, then turn off the peristaltic pump once a steady flow state is reached, and monitor and collect water head recovery data.

6) Adjust water heads on two sides to form a water head difference, put a tracer at a leftmost port, and monitor electrical conductivity in the middle and on the right side of the sandbox, where Nacl is used as an example for research in the present invention. Certainly, it is not difficult to understand that a fluorescent tracer may also be used for monitoring in another embodiment. When the fluorescent tracer is used for monitoring, the tracer tomography sandbox test can be implemented by replacing the electrical conductivity sensor with a fluorescent detection probe and a related monitoring element and sensor and using the same test operations.

7) Record and detect dynamic changes of data through a central processing unit, and form a graph in real time, analyze a test result, and finally conduct a karst structure inversion analysis with reference to program development.

In the present invention, specific settings are made according to different aquifer status and boundary conditions, steps (1) to (3) are repeated to control a flowmeter and well status, steps (4) to (6) are repeated, and a practical project is guided according to different results obtained in step (7).

The foregoing descriptions are merely preferred embodiments of this application but are not intended to limit this application. This application may include various modifications and changes for a person skilled in the art. Any modification, equivalent replacement, or improvement made without departing from the spirit and principle of this application shall fall within the protection scope of this application.

What is claimed is:

1. A sandbox test system for a karst aquifer based on tracer-hydraulic tomography inversion, the sandbox test system comprising:
    a visual sandbox apparatus including a back plate, a front plate, two porous water permeable plates, and a base, the back plate and the front plate being mounted on the base in a parallel manner;
    a water flow control apparatus including two constant water head storage tanks respectively mounted on a left side and a right side of the back plate and the front plate, one of the porous water permeable plates being mounted on the left-side constant water head storage tank, and between the back plate and the front plate, the other porous water permeable plate being mounted on the right-side constant water head storage tank, and between the back plate and the front plate, the back plate, the front plate, the porous water permeable plates, and the base define a sand layer packing space containing a sand layer;
    a karst conduit buried in the sand layer;
    a peristaltic pump;
    a plurality of horizontal wells;
    a data acquisition apparatus; and
    a data processing apparatus connected to the data acquisition apparatus, wherein:
        the two constant water head storage tanks are connected to a water supply apparatus that supplies water to the two constant water head storage tanks, so as to control water volumes of the two constant water head storage tanks;
        the front plate is provided with horizontal well mounting holes and tracer adding holes, the plurality of horizontal wells are respectively mounted in the horizontal well mounting holes, and at least one of the horizontal wells is used as a monitoring well, and at least one of the horizontal wells is used as a water injection and pumping well; and
        the water injection and pumping well is connected to the peristaltic pump, and the monitoring well is connected to a seepage pressure sensor or an electrical conductivity sensor, the electrical conductivity sensor and the peristaltic pump are connected to the data acquisition apparatus.

2. The sandbox test system according to claim 1, wherein:
    a bottom of each of the constant water head storage tanks is provided with a hole to be externally connected to an overflow tank, the overflow tank includes a first overflow tank and a second overflow tank,
    both an inlet of the first overflow tank and an inlet of the second overflow tank are connected to the water supply apparatus, and
    an outlet of the first overflow tank is connected to the left-wide constant water head storage tank, and an outlet of the second overflow tank is connected to the right-side constant water head storage tank.

3. The sandbox test system according to claim 2, wherein the first overflow tank is mounted on a first height adjustment apparatus and the second overflow tank is mounted on a second height adjustment apparatus.

4. The sandbox test system according to claim 1, wherein:
    each horizontal well includes an inner sleeve and an outer sleeve that are open at both ends, the inner sleeve being mounted in the outer sleeve, and the two sleeves are connected;
    a side wall of the outer sleeve is provided with a plurality of water inlet holes, and a sand prevention mesh is adhered to an inner wall of the outer sleeve; and
    the outer sleeve is externally connected to a hose and the seepage pressure sensor.

5. The sandbox test system according to claim 1, wherein the karst conduit includes three types: a branch conduit karst structure, a pool karst structure, and a waterfall karst structure.

6. The sandbox test system according to claim 1, wherein a sand prevention mesh is adhered to one side of each of the porous water permeable plates.

7. The sandbox test system according to claim 1, wherein both the front plate and the back plate are organic glass plates.

8. A method for simulating a natural flow and solute migration of an unconfined aquifer based on the sandbox test system according to claim 1, the method comprising the following steps:
    1) sieving testing sand according to required particle sizes and a required combination of the particle sizes;
    2) pre-fabricating a heterogeneous sand layer and the karst conduit, and hierarchically performing filling and compaction;
    3) sequentially mounting the horizontal wells and performing coring, connecting the monitoring well to the seepage pressure sensor or the electrical conductivity sensor, and connecting the water injection and pumping well to the peristaltic pump, water leakage prevention measures being required at joints;

4) connecting the seepage pressure sensor, the electrical conductivity sensor, and the peristaltic pump to the data acquisition apparatus, connecting the data acquisition apparatus to the data processing apparatus, switching on a water source to supply water to the overflow tanks and performing water leakage check;

5) adjusting a height of the overflow tanks to ensure a steady water head on a boundary, setting a boundary condition determined by a working condition, calibrating the seepage pressure sensor and the electrical conductivity sensor, and debugging the peristaltic pump;

adjusting the peristaltic pump to control a water injection and pumping speed, turning on the seepage pressure sensor or the electrical conductivity sensor before the peristaltic pump operates, and monitoring and collecting water head data in advance, to obtain an initial water head at a pumping port; and pumping at the horizontal wells during the test, simultaneously starting head monitoring to record an instantaneous water head change, turning on the peristaltic pump, then turning off the peristaltic pump once a steady flow state is reached, and monitoring and collecting water head recovery data;

6) adjusting water heads on two sides to form a particular water head difference, putting a tracer at a leftmost port, and monitoring electrical conductivity in a middle and on a right side of the sandbox apparatus; and 7) recording and detecting dynamic changes of data through a central processing unit, and forming a graph in real time, analyzing a test result, and finally conducting a karst structure inversion analysis with reference to program development.

9. The method according to claim 8, wherein specific settings are made according to different aquifer status and boundary conditions, steps (1) to (3) are repeated to control a flowmeter and well status, steps (4) to (6) are repeated, and a practical project is guided according to different results obtained in step (7).

* * * * *